United States Patent [19]
Leushner et al.

[11] Patent Number: 6,083,699
[45] Date of Patent: Jul. 4, 2000

[54] METHOD FOR BI-DIRECTIONAL SEQUENCING OF NUCLEIC ACID POLYMERS

[75] Inventors: James Leushner, North York; May Hui, West Toronto; James M. Dunn, Scarborough, all of Canada; Marina T. Larson, Yorktown, N.Y.; Jean-Michel Lacroix, Etobicoke; Robert Shipman, Mississauga, both of Canada

[73] Assignee: Visible Genetics Inc., Toronto, Canada

[21] Appl. No.: 09/009,483

[22] Filed: Jan. 20, 1998

Related U.S. Application Data

[63] Continuation-in-part of application No. 08/640,672, May 1, 1996, Pat. No. 5,789,168, application No. 08/684,498, Jul. 19, 1996, Pat. No. 5,830,657, application No. 08/807,138, Feb. 27, 1997, Pat. No. 5,888,736, and application No. PCT/US97/07134, Apr. 29, 1997.

[51] Int. Cl.$^7$ ............................................... C12Q 1/68
[52] U.S. Cl. ................................................................ 435/6
[58] Field of Search ............................. 435/6, 91.2, 194; 935/76, 77

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,729,947 | 3/1988 | Middendorf et al. | 435/6 |
| 4,795,699 | 1/1989 | Tabor et al. | 435/5 |
| 4,889,818 | 12/1989 | Gelfand et al. | 435/194 |
| 4,965,188 | 10/1990 | Mullis et al. | 435/6 |
| 5,079,352 | 1/1992 | Gelfand et al. | 538/27 |
| 5,352,600 | 10/1994 | Gelfand et al. | 435/194 |
| 5,427,911 | 6/1995 | Ruano | 435/6 |
| 5,789,168 | 8/1998 | Leushner et al. | 435/6 |

FOREIGN PATENT DOCUMENTS

| | | |
|---|---|---|
| 0265293 | 4/1988 | European Pat. Off. . |
| 0386859 | 9/1990 | European Pat. Off. . |
| 0655506 | 5/1995 | European Pat. Off. . |
| 8907149 | 8/1989 | WIPO . |
| 93/02212 | 2/1993 | WIPO . |
| 9302212 | 2/1993 | WIPO . |
| 9308305 | 4/1993 | WIPO . |
| 9426894 | 11/1994 | WIPO . |
| 9601909 | 1/1996 | WIPO . |

OTHER PUBLICATIONS

Reeve et al. A novel thermostable polymerase for DNA sequencing. Nature 376: 796–797, Aug. 1995.
Wiemann et al., "Simultaneous On–Line DNA Sequencing on Both Strands with Two Fluorescent Dyes", *Anal. Biochem.* 224: 117–121 (1995).
Olesen et al., "Chemiluminsecent DNA sequencing with multiplex labeling", *Biotechniques* 15: 480–485 (1993).
Wiemann et al., "Doublex fluorescent DNA sequencing: two independent sequences obtained simultaneously with one reaction with internal labeling an unlabeled primers", *Anal. Biochem* 234: 166–174 (1996).
Creasey et al., "Application of a novel chemiluminescence based DNA detection method to a single–vector and multiplex DNA sequencing" *Biotechniques* 11: 102–109 (1991).
Tabor et al., "A single residue in DNA Polymerases of the *Escherichia coli* DNA polymerase I family is critical for distinguishing between deoxy and dideoxynucleotides" *Proc. Nat'l Acad. Sci. USA*.92: 6339–6343 (1995).
Reeve et al., A novel thermostable polymerase for DNA sequencing *Nature* 376: 796–797 (1995).
Kambara et al, "Real Time Automated Simultaneous Double Stranded DNA Sequencing Using Two–Color Fluorophore Labeling" *Biotechnology* 9: 648–651 (1991).
Sarkar et al., "Dideoxy Fingerprinting (ddF): A rapid and Efficient Screen for the Presence of Mutations" *Genomics* 13: 441–443 (1992).
Wiemann et al., "Simultaneous On–Line Sequencing on Both Strands with Two Fluorescent Dyes" *Anal. Biochem.* 224: 117–121 (1995).
Gyllenstein et al., "Generation of single–stranded DNA by polymerase chain reaction and its application to direct sequencing of the HLA–DQA locus" *Proc. Nat'l Acad. Sci. USA* 85: 7652–7656 (1988).
Mullis et al., "Specific Synthesis of DNA in Vitro via a Polymerase–Catalyzed Chain Reaction" *Meth. Enzymol.* 155: 335–350 (1987).
Ruano et al., "Genotyping and haplotyping of polymorphisms directly from genomic DNA via coupled amplification and sequencing (CAS)" *Nucl. Acids Res.* 19: 6877–6882 (1991).
Murakawa et al., :Direct Detection of HIV–1 RNA from AIDS and ARC Patient Samples *DNA* 7: 287–295 (1988).

(List continued on next page.)

*Primary Examiner*—Nancy Degen
*Assistant Examiner*—Thomas G. Larson
*Attorney, Agent, or Firm*—Oppedahl & Larson LLP

[57] ABSTRACT

A method is provided for simultaneously determining the positions of a selected nucleotide base in a target region of both strands of a denatured duplex nucleic acid polymer. The nucleic acid polymer is combined with a reactant mixture comprising first and second oligonucleotide primers, said primers binding to the sense and antisense strands, respectively, of the nucleic acid polymer at a location flanking the target region; a thermostable DNA polymerase; a chain-terminating nucleotide triphosphate complementary to the selected nucleotide base; and other reagents for synthesis of chain extension products to form a reaction mixture. This mixture is processed through a plurality of thermal cycles, each including at least a chain extension phase and a denaturation phase to produce chain extension products. These chain extension products are evaluated to determine the positions of the selected bases. The method of the invention differs from the prior art, because the first and second oligonucleotide primers are each labeled with different, spectroscopically-distinguishable fluorescent labels. The method therefore obtains information about both DNA strands simultaneously while providing improved sensitivity as a result of the non-linear increase in the amount of DNA which results from the production of additional templates molecules from unterminated fragments.

5 Claims, 4 Drawing Sheets

OTHER PUBLICATIONS

Carothers et al., "Point Mutation Analysis in A Mammalian Gene: Rapid Preparation of Total RNA, PCR Amplification of cDNA, and Taq Sequencing by a Novel Method" *BioTechniques* 7: 494–498 (1989).

Murray, V., "Improved Double–Stranded DNA Sequencing Using the Linear Polymerase Chain Reaction", *Nucl. Acids Res.* 17: 8889 (1989).

Sanger et al., "DNA Sequencing with Chain–Terminating Inhibitors", *Proc. Nat'l Acad. Sci.* 74: 5463–5467 (1977).

Miller et al., "Chain Terminator Sequencing of Double–Stranded DNA With Built in Error Correction", General Atomics Pre–Print (1991).

Nuovo, G.J., "In situ PCR" in Dieffenbach et al., *PCR Primer: A Laboratory Manual*, pp. 235–248, Cold Spring Harbor Laboratory Press (1995).

Ruano et al., "Coupled Amplification and sequencing of genomic DNA", *Proc. Nat'l Acad. Sci (USA)* 88: 2815–2819 (1991).

Rao, V. B., "Direct–Sequencing of Polymerase Chain Reaction–Amplified DNA", *Anal Biochem*, 216: 1–14 (1994).

Kretz et al., "Cycle Sequencing" in *PCR Methods and Applications* 3: S107–S112 (1994).

Deng et al., "Simultaneous amplification and sequencing of genomic DNA (SAS): sequencing of 16S rRNA genes using total genomic DNA from *Butyrovibrio fibrisolvens*, and detection and genotyping of non–cultruable mycoplasma–like organisms directly from total DNA isolated from infected plants", *J. Microbiol. Methods* 17: 103–113 (1993).

Roemer et al., "Simultaneous Bi–Directional Cycle Sequencing", Poster presented at $9^{th}$ International Genome Sequencing and Analysis Conference, Hilton Head, SC, Sep. 1997.

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 18
      (B) TYPE: nucleic acid
      (C) STRANDEDNESS: double
      (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: primer for sequencing of exon 2 of VHL
                gene (xi) SEQUENCE DESCRIPTION: SEQ ID NO:1:

GGCTCTTTAA CAACCTTT                                                    18

(2) INFORMATION FOR SEQ ID NO: 2:

(i) SEQUENCE CHARACTERISTICS:
             (A) LENGTH: 22
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: primer for sequencing of exon 2 of VHL
                 gene (xi) SEQUENCE DESCRIPTION: SEQ ID NO:2:

GGGCTTAATT TTTCAAGTGG TC                                               22

(2) INFORMATION FOR SEQ ID NO: 3:

(i) SEQUENCE CHARACTERISTICS:
             (A) LENGTH: 17
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: primer for sequencing of exon 2 of
                 HLA-A gene (xi) SEQUENCE DESCRIPTION: SEQ ID NO:3:

GCGCCGGGAG GAGGGTC                                                     17

(2) INFORMATION FOR SEQ ID NO: 4:

(i) SEQUENCE CHARACTERISTICS:
             (A) LENGTH: 17
             (B) TYPE: nucleic acid
             (C) STRANDEDNESS: double
             (D) TOPOLOGY: linear (ii) MOLECULE TYPE: other nucleic acid (iii) HYPOTHETICAL:no

```
        (iv) ANTI-SENSE: no (v) FRAGMENT TYPE: internal (vi) ORIGINAL SOURCE:
             (A) ORGANISM: human (ix) FEATURE:
             (D) OTHER INFORMATION: primer for sequencing of exon 2 of
                 HLA-A gene (xi) SEQUENCE DESCRIPTION: SEQ ID NO:4:

GTCGTGACCT GCGCCCC                                                       17

(2) INFORMATION FOR SEQ ID NO: 5:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: primer for sequencing of exon 3 of
                 HLA-A gene (xi) SEQUENCE DESCRIPTION: SEQ ID NO:5:

GGGCGGGGCG GGGCTCGGG                                                     19

(2) INFORMATION FOR SEQ ID NO: 6:

(i) SEQUENCE CHARACTERISTICS:
             (A) LENGTH: 23
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: primer for sequencing of exon 3 of
                 HLA-A gene (xi) SEQUENCE DESCRIPTION: SEQ ID NO:6:

CGGGAGATCT ACAGGCGATC AGG                                                23

(2) INFORMATION FOR SEQ ID NO: 7:

(i) SEQUENCE CHARACTERISTICS:
             (A) LENGTH: 18
             (B) TYPE: nucleic acid
             (C) STRANDEDNESS: double
             (D) TOPOLOGY: linear
```

(ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: primer for sequencing of exon 2 of
                 HLA-B gene (xi) SEQUENCE DESCRIPTION: SEQ ID NO:7:

TCCCACTCCA TGAGGTAT                                                      18

(2) INFORMATION FOR SEQ ID NO: 8:

(i) SEQUENCE CHARACTERISTICS:
             (A) LENGTH: 17
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: primer for sequencing of exon 2 of
                 HLA-B gene (xi) SEQUENCE DESCRIPTION: SEQ ID NO:8:

GTCGTGACCT GCGCCCC                                                       17

(2) INFORMATION FOR SEQ ID NO: 9:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: primer for sequencing of exon 3 of
                 HLA-B gene (xi) SEQUENCE DESCRIPTION: SEQ ID NO:9:

GGGCGGGGCG GGGCTCGGG                                                     19

(2) INFORMATION FOR SEQ ID NO: 10:

(i) SEQUENCE CHARACTERISTICS:

```
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: primer for sequencing of exon 3 of
            HLA-B gene (xi) SEQUENCE DESCRIPTION: SEQ ID NO:10:

GAAGGCTCCC CACTGCCC                                                      18

(2) INFORMATION FOR SEQ ID NO: 11:

(i) SEQUENCE CHARACTERISTICS:
        (A) LENGTH:18
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: primer for sequencing of exon 2 of
            HLA-C gene (xi) SEQUENCE DESCRIPTION: SEQ ID NO:11:

GGAGGGTCGG GCGGGTCT                                                      18

(2) INFORMATION FOR SEQ ID NO: 12:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: primer for sequencing of exon 2 of
            HLA-C gene (xi) SEQUENCE DESCRIPTION: SEQ ID NO:12:

GTCGTGACCT GCGCCCC                                                       17
```

-continued (2) INFORMATION FOR SEQ ID NO: 13:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: primer for sequencing of exon 3 of
            HLA-C gene (xi) SEQUENCE DESCRIPTION: SEQ ID NO:13:

GACCGCGGGG GCGGGGCCA                                      19

(2) INFORMATION FOR SEQ ID NO: 14:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: primer for sequencing of exon 3 of
            HLA-C gene (xi) SEQUENCE DESCRIPTION: SEQ ID NO: 14:

GACCACGGGG GCGGGGCCA                                      19

(2) INFORMATION FOR SEQ ID NO: 15:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: primer for sequencing of exon 3 of
            HLA-C gene (xi) SEQUENCE DESCRIPTION: SEQ ID NO: 15:

GAGGCTCCCC ACTGCCC                                                          17

(2) INFORMATION FOR SEQ ID NO: 16:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of cryptic
            plasmis (xi) SEQUENCE DESCRIPTION: SEQ ID NO: 16:

TCCGGAGCGA GTTACGAAGA                                                       20

(2) INFORMATION FOR SEQ ID NO: 17:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of cryptic
            plasmid (xi) SEQUENCE DESCRIPTION: SEQ ID NO: 17:

ATTCAATGCC CGGGATTGGT                                                       20

(2) INFORMATION FOR SEQ ID NO: 18:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis -continued

```
    (ix) FEATURE:
         (D) OTHER INFORMATION: primer for sequencing of VS regions (xi) SEQUENCE DESCRIPTION: SEQ ID NO:18:

CCGACCGCGT CTTGAAAACA GATGT                                          25

(2) INFORMATION FOR SEQ ID NO: 19:

(i) SEQUENCE CHARACTERISTICS:
         (A) LENGTH: 21
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:19:

CACCCACATT CCCAGAGAGC T                                              21

(2) INFORMATION FOR SEQ ID NO: 20:

(i) SEQUENCE CHARACTERISTICS:
         (A) LENGTH: 21
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:20:

CGTGCAGCTT TGTGGGAATG T                                              21

(2) INFORMATION FOR SEQ ID NO: 21:

(i) SEQUENCE CHARACTERISTICS:
         (A) LENGTH: 24
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: Chlamydia trachomatis
```

```
    (ix) FEATURE:
         (D) OTHER INFORMATION: primer for sequencing of VS regions (xi) SEQUENCE DESCRIPTION: SEQ ID NO:21:

CTAGATTTCA TCTTGTTCAA TTGC                                              24

(2) INFORMATION FOR SEQ ID NO: 22:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:22:

AGCATGCGTR TKGGTTACTA YGG                                               23

(2) INFORMATION FOR SEQ ID NO: 23:

(i) SEQUENCE CHARACTERISTICS:
         (A) LENGTH: 24
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:23:

TGACTTTGTT TTCGACCGYG TTTT                                              24

(2) INFORMATION FOR SEQ ID NO: 24:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
```

(A) ORGANISM: Chlamydia trachomatis (ix) FEATURE:
            (D) OTHER INFORMATION: primer for sequencing of VS regions (xi) SEQUENCE DESCRIPTION: SEQ ID NO:24:

CTAAAGTYGC RCATCCACAT TCC                                               23

(2) INFORMATION FOR SEQ ID NO: 25:

(i) SEQUENCE CHARACTERISTICS:
            (A) LENGTH: 23
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:25:

CATCCACATT CCCASARAGC TGC                                               23

(2) INFORMATION FOR SEQ ID NO: 26:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of cryptic
                  plasmid (xi) SEQUENCE DESCRIPTION: SEQ ID NO:26:

ATGCCCGGGA TTGGTTGATC                                                   20

(2) INFORMATION FOR SEQ ID NO: 27:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: Chlamydia trachomatis (ix) FEATURE:
             (D) OTHER INFORMATION: primer for sequencing of VS regions (xi) SEQUENCE DESCRIPTION: SEQ ID NO:27:

GGAGACTTTG TTTTCGACCG                                                     20

(2) INFORMATION FOR SEQ ID NO: 28:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: Chlamydia trachomatis (ix) FEATURE:
             (D) OTHER INFORMATION: primer for sequencing of VS regions (xi) SEQUENCE DESCRIPTION: SEQ ID NO:28:

CATTCCCACA AAGCTGCGCG                                                     20

(2) INFORMATION FOR SEQ ID NO: 29:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: Chlamydia trachomatis (ix) FEATURE:
             (D) OTHER INFORMATION: primer for sequencing of VS regions (xi) SEQUENCE DESCRIPTION: SEQ ID NO:29:

TTCCCACAAA GCTGCGCGAG                                                     20

(2) INFORMATION FOR SEQ ID NO: 30:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:30:

CCCACAAAGC TGCGCGAGCG                                                   20

(2) INFORMATION FOR SEQ ID NO: 31:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: HIV-1

(ix) FEATURE:
            (D) OTHER INFORMATION: primer for sequencing of HIV-1 protease
                gene (xi) SEQUENCE DESCRIPTION: SEQ ID NO:31:

ATCACTCTTT GGCAACGACC                                                   20

(2) INFORMATION FOR SEQ ID NO: 32:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: HIV-1

(ix) FEATURE:
            (D) OTHER INFORMATION: primer for sequencing of HIV-1 protease
                gene (xi) SEQUENCE DESCRIPTION: SEQ ID NO:32:

CAGGAGCAGA TGATACAGTA TTAG                                              24

(2) INFORMATION FOR SEQ ID NO: 33:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL:no -continued

```
    (iv) ANTI-SENSE: no (v) FRAGMENT TYPE: internal (vi) ORIGINAL SOURCE:
        (A) ORGANISM: HIV-1

(ix) FEATURE:
        (D) OTHER INFORMATION: primer for sequencing of HIV-1 protease
            gene (xi) SEQUENCE DESCRIPTION: SEQ ID NO:33:

CCATTCCTGG CTTTAATTTT ACTGG                                            25
```

METHOD FOR BI-DIRECTIONAL SEQUENCING OF NUCLEIC ACID POLYMERS

This application is a continuation-in-part of pending U.S. patent applications Ser. Nos. 08/640,672 filed May 1, 1996, now U.S. Pat. No. 5,789,168, 08/684,498 filed Jul. 19, 1996 now U.S. Pat. No. 5,830,657, and 08/807,138 filed Feb. 27, 1997, now U.S. Pat. No. 5,888,736 and of International Patent Application No. PCT/US97/07134 filed Apr. 29, 1997 designating the United States, and published as International Publication No. WO 97/41259 on Nov. 6, 1997, all of which are incorporated herein by reference.

BACKGROUND OF THE INVENTION

This application relates to DNA sequencing reactions, and in particular to improved bi-directional sequencing reaction protocols making use of thermally stable polymerase enzymes.

DNA sequencing can be performed in two distinct environments: a research environment in which each procedure is fairly unique and in which the sequence being determined is generally not known prior to completion of the sequence determination; and a diagnostic environment in which the same procedure is repeated on many samples and the sequences being determined are generally known. While the basic procedures used in these two environments can be the same, requirements for speed, cost-effectiveness and low risk of error in the diagnostic environment make many of the techniques actually employed in research too cumbersome to permit their effective utilization. This has limited the availability of sequencing-based diagnostics, and has indeed led some to question whether sequencing can ever be cost effective for routine diagnostic use.

The ideal DNA sequencing procedure for use in a diagnostic environment would have the following characteristics: (1) it would be able to utilize a DNA-containing sample which had been subjected to only minimal pretreatment to make the DNA accessible for sequencing; (2) it would require combining this sample with only a single reaction mixture, thus reducing risk of error and contamination, and increasing the ease with which the procedure can be automated; and (3) it would require a short amount of time to perform the sequence determination, thus decreasing the marginal costs in terms of equipment and labor for performing the test.

DNA sequencing, whether for research or diagnostics, is generally performed using techniques based on the "chain termination" method described by Sanger et al., *Proc. Nat'l Acad. Sci. (USA)* 74(12): 5463–5467 (1977). Basically, in this process, DNA to be tested is isolated, rendered single stranded, and placed into four vessels. In each vessel are the necessary components to replicate the DNA strand, i.e., a template-dependant DNA polymerase, a short primer molecule complementary to a known region of the DNA to be sequenced, and the standard deoxynucleotide triphosphates (dNTP's) commonly represented by A, C, G and T, in a buffer conducive to hybridization between the primer and the DNA to be sequenced and chain extension of the hybridized primer. In addition, each vessel contains a small quantity of one type (i.e., one species) of dideoxynucleotide triphosphate (ddNTP), e.g. dideoxyadenosine triphosphate (ddA).

In each vessel, the primer hybridizes to a specific site on the isolated DNA. The primers are then extended, one base at a time to form a new nucleic acid polymer complementary to the isolated pieces of DNA. When a dideoxynucleotide triphosphate is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

As Church and Gilbert observed, "in a mammalian cell, the DNA corresponding to any gene sequence is surrounded by DNA corresponding to some million other sequences." "The Genomic Sequencing Technique" in *Medical Genetics: Past, Present and Future,* Alan R. Liss, Inc., pp. 17–21, (1991). The same is true, to a greater or lesser extent, of any complex DNA sample, e.g. containing microbial genetic materials, plant genetic materials, complete cDNA libraries etc. In the past, DNA sequencing procedures have dealt with this complexity by adding steps which substantially purify the DNA of interest relative to other DNA species present in the sample. This purification has been accomplished by cloning of the DNA to be sequenced prior to sequencing, or by amplification of a selected portion of the genetic material in a sample to enrich the concentration of a region of interest relative to other DNA. For example, it is possible to amplify a selected portion of a gene using a polymerase chain reaction (PCR) as described in U.S. Pat. Nos. 4,683,194, 4,683,195 and 4,683,202, which are incorporated herein by reference. This process involves the use of pairs of primers, one for each strand of the duplex DNA, that will hybridize at a site located near a region of interest in a gene. Chain extension polymerization (without a chain terminating nucleotide) is then carried out in repetitive cycles to increase the number of copies of the region of interest many times. The amplified polynucleotides are then separated from the reaction mixture and used as the starting sample for the sequencing reaction. Gelfand et al. have described a thermostable enzyme, "Taq polymerase," derived from the organism *Thermus aquaticus,* which is useful in this amplification process. (See U.S. Pat. Nos. 4,889,818; 5,352,600 and 5,079,352 which are incorporated herein by reference) Taq polymerase has also been disclosed as useful in sequencing DNA when certain special conditions are met. U.S. Pat. No. 5,075,216, incorporated herein by reference.

Improvements to the original technique described by Sanger et al. have included improvements to the enzyme used to extend the primer chain. For example, Tabor et al. have described enzymes such as T7 DNA polymerase which have increased processivity, and increased levels of incorporation of dideoxynucleotides. (See U.S. Pat. No. 4,795, 699 and EP-A-0 386 857, which are incorporated herein by reference). More recently, Reeve et al. have described a thermostable enzyme preparation, called THERMO SEQUENASE™, with improved qualities for DNA sequencing. *Nature* 376: 796–797 (1995); EP-A-0 655 506, which is incorporated herein by reference. For sequencing, the THERMO SEQUENASE™ product is used with an amplified DNA sample containing 0.5–2 µg of single stranded DNA (or 0.5 to 5 µg of double stranded DNA) into four aliquots, and combining each aliquot with the THERMO SEQUENASE™ enzyme preparation, one dideoxynucleotide termination mixture containing one ddNTP and all four dNTP's; and one dye-labeled primer which will hybridize to the DNA to be sequenced. The mixture is placed in a thermocycler and run for 20–30 cycles of annealing, extension and denaturation to produce measurable amounts of dye-labeled extension products of varying lengths which are then evaluated by gel electrophoresis. EP-A-0 655 506 further asserts that THERMO SEQUENASE™ and similar enzymes can be used for amplification reactions.

Other improvements on the Sanger process have involved the use of fluorescent labels rather than radiolabels to permit real time detection. See, U.S. Pat. No. 5,171,534 of Smith et al. and U.S. Pat No. 4,729,947 of Middendorf et al. which are incorporated herein by reference. Fluorescent labels has also ben used to provide simultaneous sequencing of both strands of as DNA molecule. Wiemann et al., "Simultaneous On-Line DNA Sequencing on Both Stands with Two Fluorescent Dyes," *Anal. Biochem* 224: 117–121 (1995).

Notwithstanding the basic desirability of simplifying the sequencing reaction procedures to minimize risk of error and contamination, efforts to combine the amplification reaction and the sequencing reaction into a single step have been limited. One such technique has been called "cycle sequencing" or "linear amplification sequencing." In this technique, a thermostable polymerase and dideoxynucleotide triphosphates are used in a thermocycled reaction to produce sequencing fragments. The reaction differs from PCR amplification in that only one primer is used, so there is only a linear increase in the amount of DNA with each cycle. Kretz et al., in *PCR Methods and Applications*, Cold Spring Harbor Press, pp S107–112 (1994).

Ruano and Kidd, *Proc. Nat'l. Acad. Sci. (USA)* 88: 2815–2819 (1991) and U.S. Pat. No. 5,427,911, which are incorporated herein by reference, describe a process which they call "coupled amplification and sequencing" (CAS) for sequencing of DNA. In this process, a sample is treated in a first reaction stage with two primers and amplified for a number of cycles to achieve 10,000 to 100,000-fold amplification. A ddNTP is then added during the exponential phase of the amplification reaction, and the reaction is processed for additional thermal cycles to produce chain-terminated sequencing fragments. Sequencing of each strand is done separately.

It is an object of the present invention to provide an improved method for bi-directional sequencing of DNA samples which is well-suited for use in the diagnostic environment and for automation.

It is a further object of the invention to provide a method for bi-directional sequencing of DNA which utilizes a DNA-containing sample which has been subjected to only minimal pretreatment to make the DNA accessible for sequencing.

It is still a further object of the invention to provide a method for bi-directional sequencing of DNA which requires combining a complex DNA-containing sample with only a single reaction mixture, thus reducing risk of error and contamination, and increasing the ease with which the procedure can be automated.

SUMMARY OF THE INVENTION

The present invention provides a method for bi-directional sequencing a region of interest in a DNA sample. The method can be carried out using a single set of reagents which is added to a minimally-treated sample to produce useful sequencing results.

Thus, in accordance with the invention, a method is provided for simultaneously determining the positions of a selected nucleotide base in a target region of both strands of a denatured duplex nucleic acid polymer. The nucleic acid polymer is combined with a reactant mixture comprising first and second oligonucleotide primers, said primers binding to the sense and antisense stanrds, respectively, of the nucleic acid polymer at a location flanking the target region; a thermostable DNA polymerase; a chain-terminating nucleotide triphosphate complementary to the selected nucleotide base; and other reagents for synthesis of chain extension products to form a reaction mixture. This mixture is processed through a plurality of thermal cycles, each including at least a chain extension phase and a denaturation phase to produce chain extension products. These chain extension products are evaluated to determine the positions of the selected bases. The method of the invention differs from the prior art, because the first and second oligonucleotide primers are each labeled with different, spectroscopically-distinguishable fluorescent labels. The method therefore obtains information about both DNA strands simultaneously while providing improved sensitivity as a result of the non-linear increase in the amount of DNA which results from the production of additional templates molecules from unterminated fragments.

DETAILED DESCRIPTION OF THE INVENTION

Figure 1:
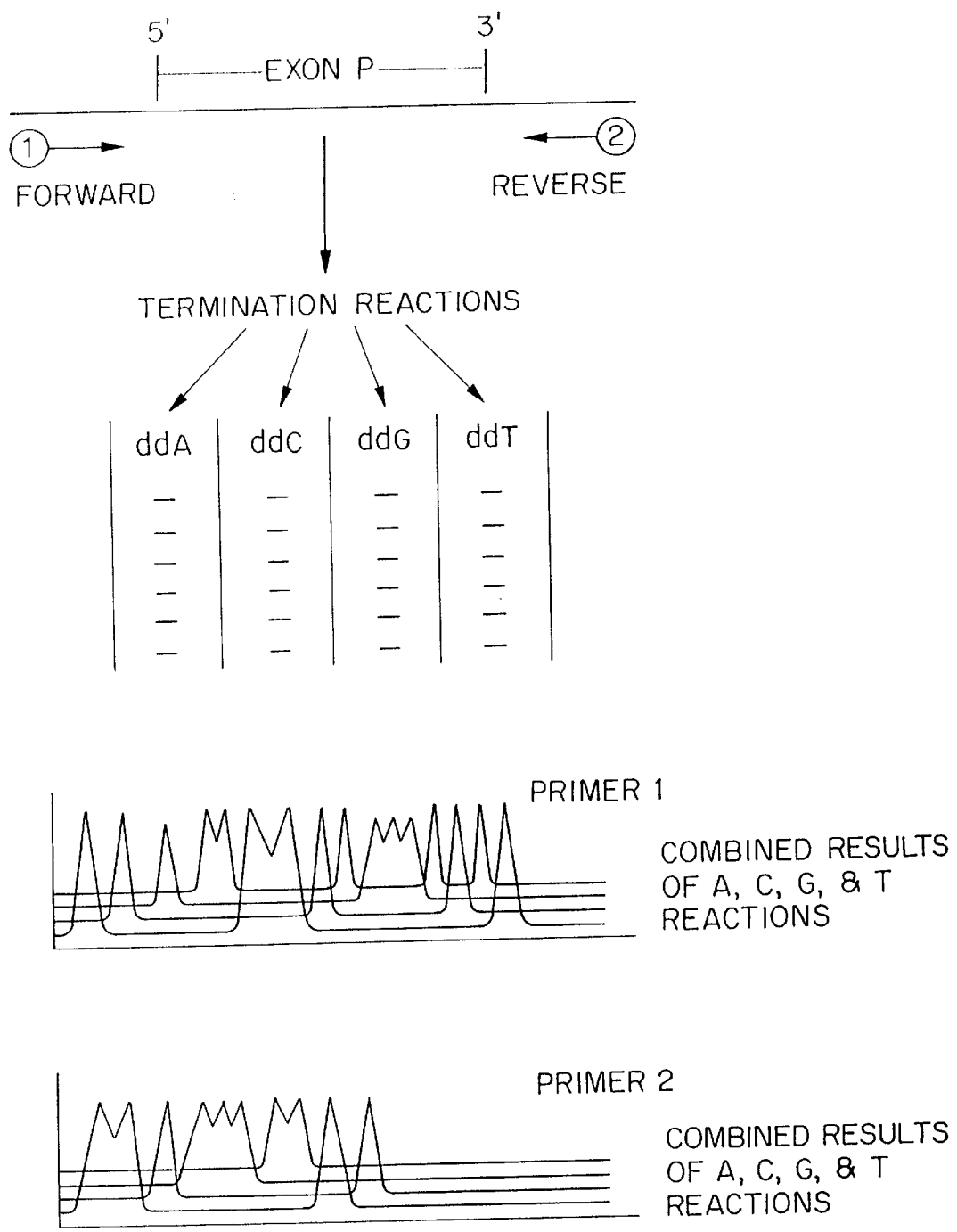
FIG. 1 illustrates the method of the invention schematically.

The present invention answers the need for a simple and readily-automated bi-directional sequencing procedure which can be used directly on samples which contain complex mixtures of DNA. To distinguish such mixtures from DNA preparations which have been sequenced in the past, the specification and claims of this application use the term "natural abundance sample" to describe such a mixture. Of course, the method of the invention is also applicable to bi-directional sequencing of less challenging samples in which the target DNA sequence has been preferentially enriched by means such as cloning or PCR amplification.

As used herein a "natural abundance sample" is a sample which has been treated to make DNA in the sample accessible for hybridization with oligonucleotide primers, for example by lysis, centrifugation to remove cellular debris and proteolytic digestion to expose the DNA, but which has not been subjected to a preferential purification or amplification step to increase the amount of target DNA relative to non-target DNA present in the initial sample. The term "natural abundance" does not, however, require the presence of all the DNA from the original sample. Thus, a complex sample containing just nuclear DNA, or just mitochondrial DNA or some subfraction of nuclear or mitochondrial DNA obtained by isolation from a tissue sample but not subjected to preferential amplification would be a "natural abundance" sample within the meaning of that term in the specification and claims of this application. The term "natural abundance" would also include a DNA sample prepared by conversion, for example by reverse transcription, of a total mRNA preparation or the genome of an RNA virus to cDNA; DNA isolated from an individual bacterial colony growing on a plate or from an enriched bacterial culture; and a viral DNA preparation where substantially the entire viral genome is isolated. The term "natural abundance" does not encompass a sample in which the isolated DNA is not a complex combination of DNA molecules, and thus would not encompass, for example, a purified plasmid preparation containing only a single species of plasmid.

Natural abundance samples of mammalian DNA can be prepared from fluid samples, e.g., blood or urine or tissue samples by any of a number of techniques, including lysis, centrifugation to remove cellular debris and proteolytic digestion to expose the DNA; salt precipitation or standard SDS-proteinase K-phenol extraction. Natural abundance samples can also be prepared using kits, for example the Gentra PURE GENE DNA Isolation Kit.

When working with natural abundance samples, the method of the invention utilizes the properties of enzymes like THERMO SEQUENASE™, namely the ability to incorporate dideoxynucleotides into an extending polynucleotide at a rate which is no less than about 0.4 times the rate of incorporation of deoxynucleotides, to provide a method for the sequencing of a nucleic acid polymer from a natural abundance sample in a single set of thermocycling reactions which can be carried out in a single vessel. Other thermostable polymerase enzymes, including Taq polymerase and VENT polymerase can be used for less challenging samples.

FIG. 1 illustrates the method of the invention in flow chart form. As shown in FIG. 1, a sample containing a target nucleic acid polymer which includes a region to be sequenced is combined with a reaction mixture containing two primers labeled with different labels, a mixture of dNTP's, a chain terminating nucleotide triphosphate, i.e., a dideoxynucleotide triphosphate, and a thernostable polymerase. The mixture is processed for a number of thermal cycles sufficient to produce detectable amounts of sequencing fragments, generally from 20 to 50 cycles. During each cycle, the primers each anneal to the respective strand of target DNA present in the sample, and primer chain extension using the polymerase enzymes and the nucleotide triphosphate feedstocks proceeds until terminated by incorporation of a chain-terminating nucleotide triphosphate. This results in the production of sequencing fragments comparable to those generated in a conventional sequencing reaction. Analysis of these fragments provides information concerning the sequence of the selected region of the target DNA. Those extension products which are not terminated prior to reaching the region complementary to the other primer can serve as template for generation of sequencing fragments in later cycles, although this generally occurs to a very small extent. Finally, the product mixture containing dideoxy-terminated fragments is loaded onto an electrophoresis gel for analysis of the positions of the base corresponding to the chain-terminating nucleotide triphosphate with in the target nucleic acid polymer.

The method of the invention as illustrated obtains both the forward and reverse sequences of a target nucleic acid sequence by using two primers, each with a spectroscopically-distinguishable label. The sample, preferably a natural abundance sample, is mixed with forward and reverse primers, each with a distinguishable label (1 and 2). The reaction is performed with four termination reactions, one each for A, C, G and T. Each reaction is loaded into a single well of an automated sequencing instrument that detects and distinguishes at least the two labels employed. The results detected from label 1 are combined to give the forward sequence. The results detected from label 2 are combined to give the reverse sequence. The two sequences can be used to check each other and correct any ambiguities in base calling. In addition, the opposite sequence can be used to confirm sequence proximal to a primer which is found empirically to be difficult to determine on commercially available automated DNA sequencers.

The absolute and relative amounts of nucleotide triphosphates and chain-terminating nucleotide triphosphates may be optimized for the particular enzyme employed. In actual practice, it has been found that useful results are obtained with THERMO SEQUENASE™ when the reaction is run for 35 to 45 cycles, using a dideoxy:deoxy mole ratio of 1:100 to 1:300. In general, each nucleotide triphosphate will be included in the reaction mixture at concentrations of from 250 $\mu$M to 1.5 mM, and the chain-terminating nucleotide triphosphate will be included at a level of from 0.5 $\mu$M to 30 $\mu$M to produce compositions in which the mole ratio of the chain terminating nucleotide triphosphate to the corresponding nucleotide triphosphate is from 1:50 to 1:1000, preferably from 1:100 to 1:500. This will result in incorporation of a chain-terminating nucleotide triphosphate into from 30 to almost 100 percent of the extending polymer chains formed during the thermal cycling of the reaction mixture.

In the method of the invention, a natural abundance sample containing, or suspected to contain, a target DNA sequence is combined in a reaction mixture with an appropriate polymerase, all four types of deoxynucleotide triphosphates, a dideoxynucleotide triphosphate, and first and second primers. The primers used in the method of the present invention can be any pair of primers which hybridize with the sense and antisense strands of the target DNA flanking a selected region that is to be sequenced, and which do not both hybridize to neighboring locations in human DNA or other DNA potentially found in the sample. As used herein, the term "flanking" will be understood to mean the positioning of primers at the 5'-ends of the selected region on each DNA strand, such that extension of the primers leads to replication of the region between the primers. The primers are preferably selected such that the primer pair flanks a region that is about 500 bp or less, although primers spanning larger regions of DNA can be utilized with adjustments to the sequencing mixture (generally an increase in the relative amount of deoxynucleotide triphosphates) to increase the amount of longer sequencing fragments produced.

Primers can be selected to hybridize with highly conserved regions which are the same in all variants of the target DNA or can be prepared as degenerate primers to take known sequence variations at the primer site into account. Thus, the first and second primers of the invention may each be a discrete oligonucleotide species, or may be a set of oligonucleotide primers with similar but not identical sequences.

Both of the primers used in the method of the invention are labeled with a detectable label at the 5'-end thereof, particularly with a fluorescent label such as fluorescein or a cyanine dye such as Cy 5.5. The labels selected should be spectroscopically-distinct, i.e., they should have either a different excitation spectrum or a different emission spectrum such that one primer can be distinguished from the other. The two different fluorophores as in the process described by Wiemann et al., "Simultaneous On-Line DNA Sequencing on Both Stands with Two Fluorescent Dyes," *Anal. Biochem* 224: 117–121 (1995) can suitably be used in the method of the invention to determine the sequence of both strands of the sample DNA in a single reaction.

The nucleotide triphosphate feedstock mixture is a standard mixture of the four conventional deoxynucleotide bases (A, C, G and T) in a buffer suitable for template-dependent primer extension with the enzyme employed. As will be appreciated by persons skilled in the art, the specific concentrations of the nucleotide triphosphates and the nature of the buffer will vary depending on the enzyme employed. Standard buffers and reagent concentrations for various known polymerase enzymes may be employed in the invention.

The reaction mixture used in the present invention also includes one type (or one species) of chain-terminating nucleotide triphosphate. Separate reactions for the four different types of bases may be run either concurrently or successively. Running all four bases concurrently comports with conventional sequencing practice. However, a preferred embodiment of the present invention combines the single vessel methodology of this application with "single track sequencing" which is described in commonly assigned U.S. patent application Ser. No. 08/577,858, which is incorporated herein by reference. In single track sequencing, the determination of the positions of only one (or in any event less than 4) nucleotide(s) of a target sequence is frequently sufficient to establish the presence of and determine the qualitative nature of a target microorganism by providing a finger-print or bar-code of the target sequence that may be sufficient to distinguish it from all other known varieties of the sequence. Throughput is increased by reducing the number of reactions and electrophoresis runs required to identify a sequence. By selection of the order of bases tested, and intermediate analysis, it may be unnecessary to run all four bases to determine the presence and specific qualitative nature of any target microorganism present in the sample.

The present method can be used in combination with any type of detection system that is compatible with the labels employed on the primers. For example, the sample can be processed on multiple instruments (a Pharmacia A.L.F. sequencer may be employed when fluorescein-labeled primers are used, while a Visible Genetics MICROGENE BLASTER is appropriate when the label used is Cy5.5), or it can be evaluated on an instrument which is capable of detecting signals from multiple labels. An example of such an instrument is the Prism 377 Sequencer (Applied Biosystems Inc.) which detects and distinguishes between 4 dyes in a single lane. Spectroscopically distinguishable dyes which are recognized by the Prism 377 are the FAM, ROX, TAMRA and JOE dyes known in the art.

Figure 2A:
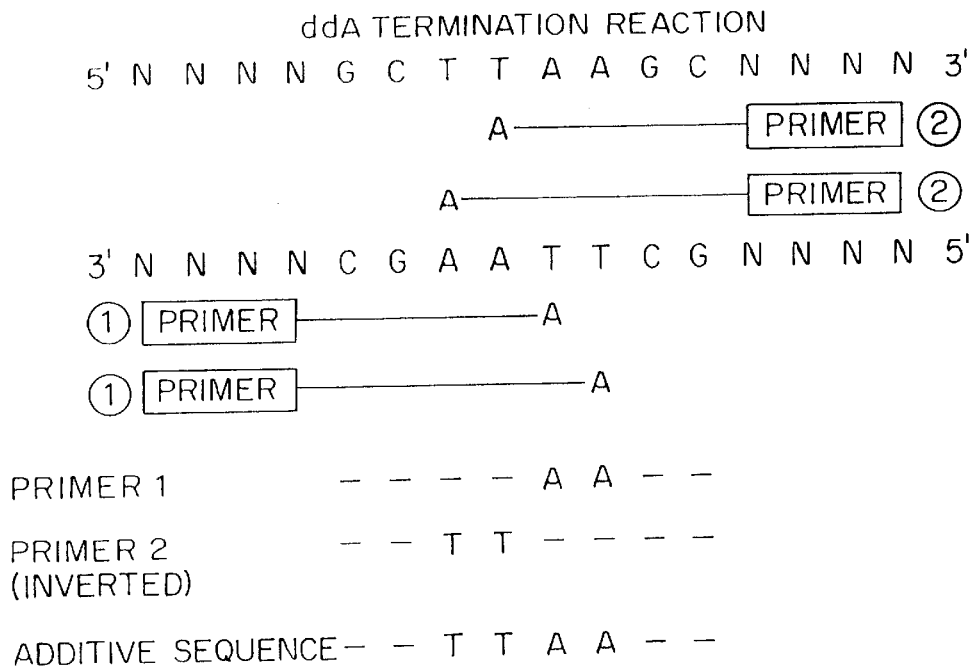
FIGS. 2A and 2B illustrate an embodiment of the invention.

The present invention also permits an improvement in the throughput achievable with an instrument by taking advantage of the fact that a single ddA termination reaction identifies the A nucleotides from each strand, FIG. 2A, thus identifying the complementary base (in this case T) in the opposite strand. (i.e. the A termination sites on the opposite strand correspond to T nucleotide sites in the first strand). The complementary base can be located in the "missing" sites of the opposite strand. Note that sequence from the opposite strand must be inverted before it can be added in to the missing sites because it starts at the opposite end of the target gene and chain extension is in the opposite direction.

Figure 2B:
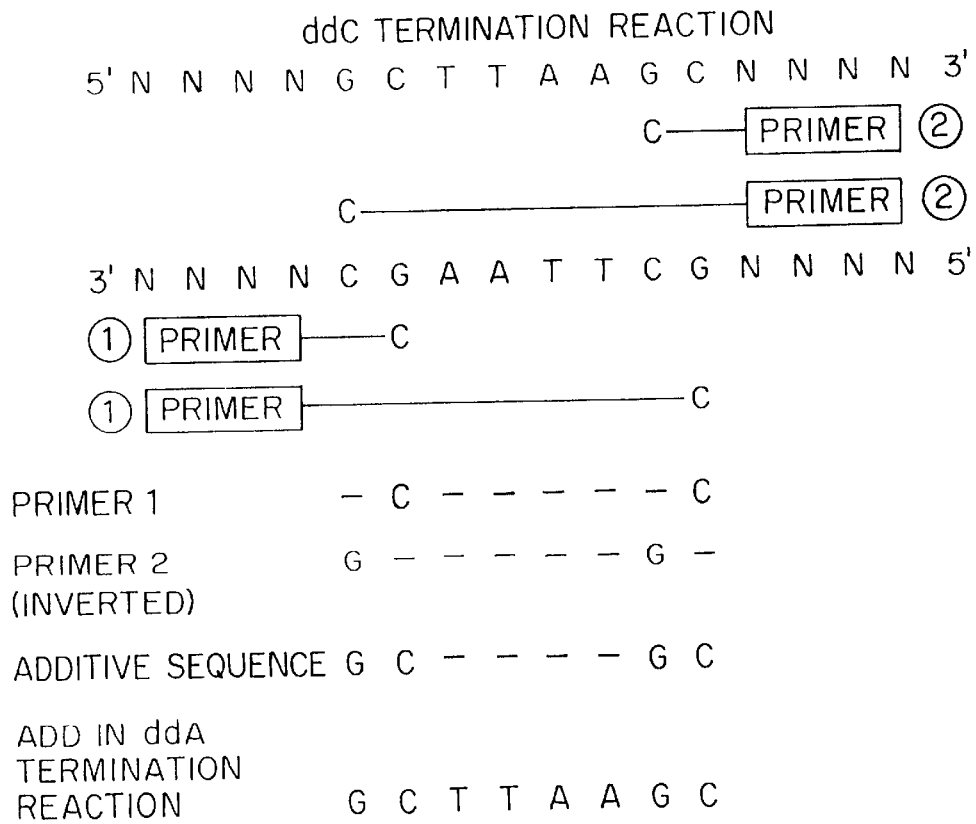

In FIG. 2B, a second termination reaction for ddC is added. This allows identification of C and its complement G in each strand. When these results are added to the first reaction, a full DNA sequence is obtained. Thus on the basis of 2 termination reactions employing one ddNTP chain terminator each, the full 4 lane sequence of a gene can be obtained.

The base-calling and compiling of sequences illustrated in FIG. 2A and 2B can be facilitated using GENEOBJECTS software (Visible Genetics Inc., Toronto) and employing techniques disclosed in U.S. patent application Nos. 08/497,202 and 08/670,534, incorporated herein by reference.

The method of the present invention is advantageously applied in many contexts including: (1) detection of mutations, particularly mutations of medical significance, in samples derived from a human patient, animal, plant or microorganism; (2) determination of HLA type ancillary to transplant procedures; (3) detection and identification of microorganisms, particularly pathogenic microorganisms, in a sample; and (4) in-situ sequencing reactions to produce sequencing fragments within a histological specimen which are then removed from a selected location on the tissue preparation and loaded onto a gel for sequence analysis. This latter approach is particularly useful for evaluation of archived samples in retrospective studies where the outcome of a disease condition is known, but the potentially causative mutation is not. This method can be used with labeled primers for single base sequencing (or multiple-base sequencing using multiple tissue samples).

The basic method of the invention can also be enhanced by various modifications without departing from the scope of the present invention. For example, improvements in reproducibility and sensitivity can be obtained by using a combination of an enzyme having a high affinity for incorporation of dideoxynucleotide triphosphates into the extending polymer, e.g., THERMO SEQUENASE™, and one having a low affinity for incorporation of dideoxynucleotide triphosphates into the extending polymer, e.g., Taq polymerase, under conditions where both enzymes are actively catalyzing template-dependent primer extension polymerization. As noted above, the high affinity enzyme produces almost entirely termination products, with very few of the polymers actually being extended to full length. On the other hand, the low affinity enzyme produces almost exclusively full length product, with relatively few termination products. Addition of the low affinity enzyme to the reaction mixture increases the sensitivity of the method by producing more full length material to be sequenced without increasing the processing time or adding processing steps. The increase in sensitivity can be controlled by varying the ratio of high affinity to low affinity enzyme present in the mixture.

It will be noted, however, that including of low affinity enzyme to produce full length product will also result in the formation of a very intense labeled full-length product peak. This peak may make analysis of the bases near the end of the sequence difficult. To obtain the benefits of increased sensitivity while making less full length product, it may be desirable to utilize a low affinity enzyme which is more thermolabile than Taq polymerase, such that the low affinity enzyme is essentially inactivated by the end of the first 15 to 25 cycles. This would allow the production of longer fragments early in the assay and the generation of more terminated fragments late in the assay.

The reaction mixture of the invention may also incorporate other additives which enhance the formation of sequencing fragments. For example, a product called TaqStart™ Antibody is a monoclonal antibody which binds to and blocks the activities of Taq polymerase. This antibody is added to PCR reactions using Taq polymerase to block enzyme activity during set-up at ambient temperature to prevent or reduce the formation of non-specific amplification products. TaqStart™ Antibody can be used in the present invention with THERMO SEQUENASE™ to reduce nonspecific primer extension reactions.

Other materials which can be used in the reaction mixture of the invention are uracil-DNA glycosylases and corresponding unconventional nucleotides as described in U.S. Pat. No. 5,418,149, incorporated herein by reference, to reduce non-specific product formation. Roche sells a product under the trademark AMPERASE™ which can be used conveniently for this purpose. The method of the invention may also be used in conjunction with Johnson & Johnson techniques known as "PCR IN A POUCH" which is described in U.S. Pat. No. 5,460,780 incorporated herein by reference.

EXAMPLE 1

The DNA sequence of exon 2 of the VHL gene was sequenced from a human DNA sample using the method of the invention as follows.

A natural abundance sample was prepared from a human patient blood sample using the Gentra PURE GENE DNA isolation kit according to the manufacturers instructions. Briefly, in the procedure, the blood cells were lysed, centrifuged to recover the lysed white blood cells and mixed with proteinase K. Protein is then separated from the sample by precipitation and the remaining nucleic acids are precipitated and collected.

|  | final amt. | final vol. |
|---|---|---|
| DNA | 175 ng | 3.5 ul |
| 5' Primer (Cy5.5 labeled) 1pmol/ul | 3 pmol | 3.0 ul |
| 3' Primer (Fluorescein labeled) 1pmol/ul | 3 pmol | 3.0 ul |
| DMSO 100% |  | 1.5 ul |
| 10X ThermoSequenase Reaction Buffer (Amersham) |  | 2.0 ul |
| ThermoSequenase Enzyme 32U/ul   6.4 U | 0.2 ul |  |
|  |  | 13.2 ul |

```
5' primer
5'-GGCTCTTTAA CAACCTTT-3'      [SEQ. ID No.: 1] (Cy5.5 labeled)
3' primer
5'-GGGCTTAATT TTTCAAGTGG TC-3' [SEQ. ID No.: 2] (Fluorescein labeled)
```

The fluorescent label indicated is conjugated to the 5' end of the primer oligonucleotide by means known in the art. Briefly, this may include phosphoramidite technology commonly employed on automated DNA synthesizers, or a two stage reaction where an amino linker is added to the 5' end of the primer oligonucleotide and condensed with a dye-ester conjugate. The fluorescent dye is selected according to the requirements of the detection device employed.

3 µl aliquots of the reaction mixture were placed into each of 4 tubes containing 3 µl of one of the following termination mixes containing all 4 dNTPs and one of the following ddNTPs: A, C, G or T (dNTP/ddNTP=100:1 ratio; 750 µM: 7.5 µM) after which the mixture was layered with oil. The mixture was then processed in a PTC 100 Thermocycler as follows:

```
denature
95° C. 120 sec
35 cycles
95° C. 50 sec
52° C. 30 sec
70° C. 60 sec
finish
70° C. 120 sec
6° C. soak
```

Figure 3A:
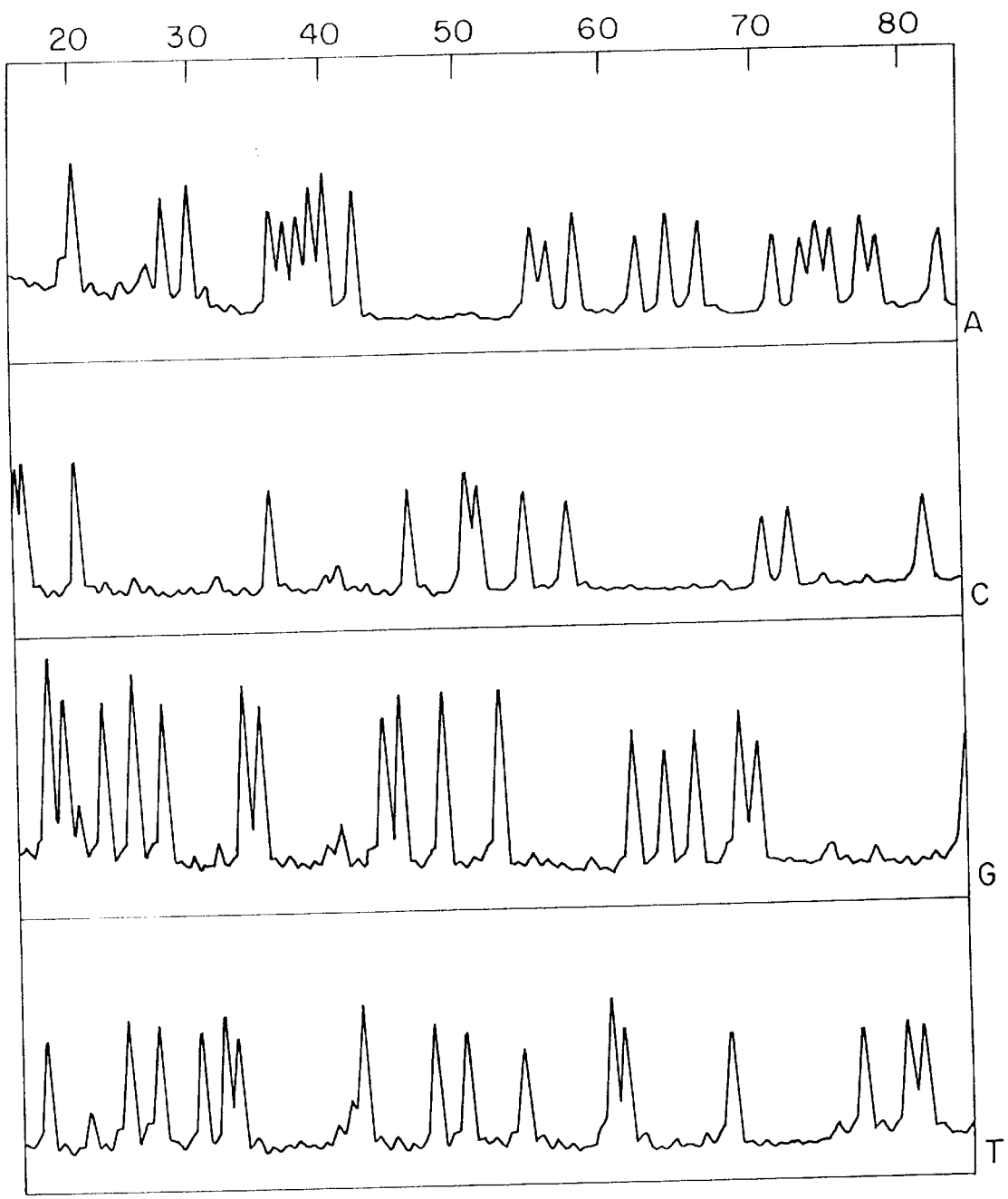
FIGS. 3A and 3B show results for a sequencing determination using the method according to the invention.
Figure 3B:
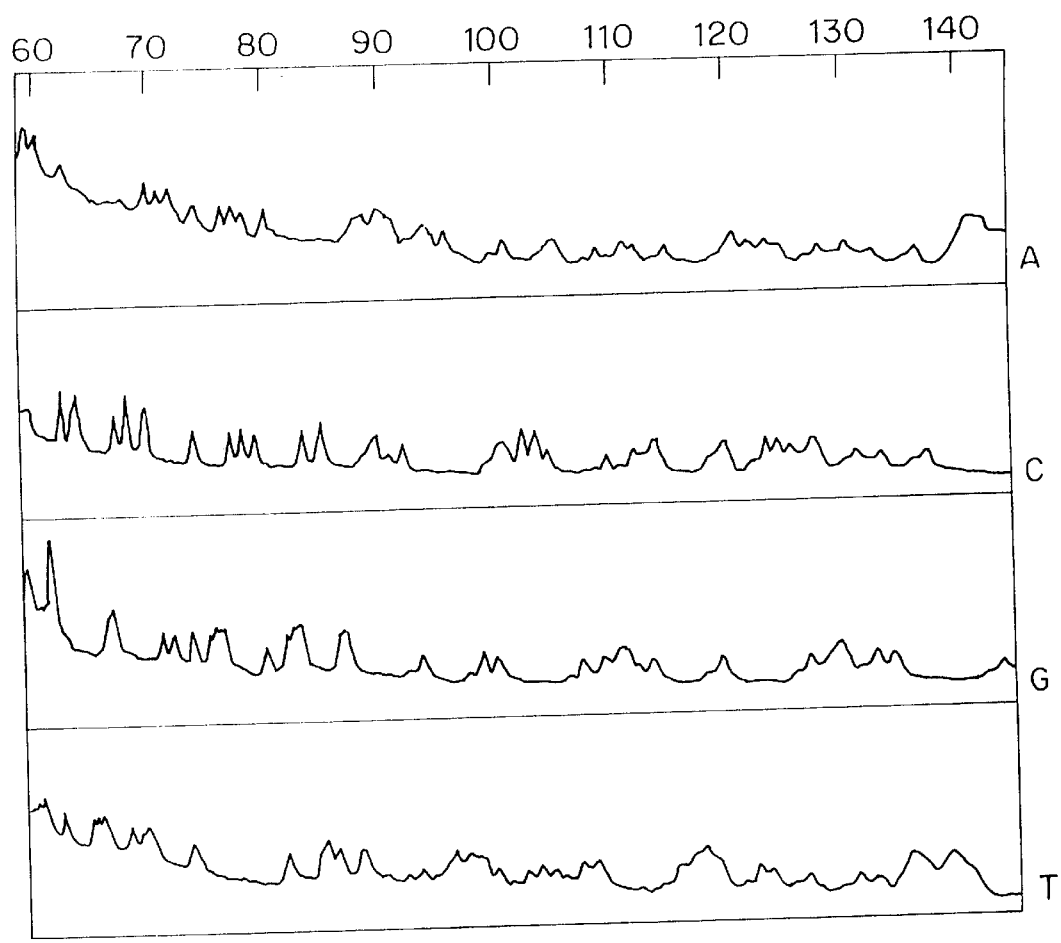

6 µl dye/stop solution was then added to each tube to make a final volume of 12 µl. 2 µl of final mixture was loaded on a lane of the MICROGENE BLASTER. 7 µl of final mixture was loaded on a lane of an ALF automated Sequencer (Pharmacia). Electrophoresis was performed and the separated reaction products were detected, recorded and evaluated. FIGS. 3A and B show the results obtained with the MICROGENE BLASTER which detects the Cy5.5-labeled product and the A.L.F. which detects the fluorescein-labeled product, respectively.

EXAMPLE 2

A human natural abundance DNA sample is prepared from a patient blood sample using the Gentra Pure Gene DNA isolation kit according to the manufacturers instructions. Briefly, in the procedure, the blood cells were lysed, centrifuged to recover the lysed white blood cells and mixed with proteinase K. Protein is then separated from the sample by precipitation and the remaining nucleic acids are precipitated and collected.

The natural abundance sample is combined in a reaction mixture for characterization of the HLA type of the sample as follows:

|  |  | final amt. | final vol. |
|---|---|---|---|
| DNA (natural abundance) |  | 175 ng | 3.5 ul |
| 5' Primer (Cy5.5 labeled) | 1 pmol/ul | 3 pmol | 3.0 ul |
| 3' Primer (Fluorescein labeled) | 1 pmol/ul | 3 pmol | 3.0 ul |
| DMSO | 100% |  | 1.5 ul |
| 10X THERMO SEQUENASE Reaction Buffer (Amersham) |  |  | 2.0 ul |
| THERMO SEQUENASE Enzyme | 32 U/ul | 6.4 U | 0.2 ul |
|  |  |  | 13.2 ul |

The fluorescent label indicated is conjugated to the 5' end of the primer oligonucleotide by means known in the art. Briefly, this may include phosphoramidite technology commonly employed on automated DNA synthesizers, or a two stage reaction where an amino linker is added to the 5' end of the primer oligonucleotide and condensed with a dye-ester conjugate. The fluorescent dye is selected according to the requirements of the detection device employed.

The primer pair for a specific HLA gene may be selected from the following non-exclusive list:

HLA-A

EXON2
5' Primer
vgiawsp1   GCGCCGGGAGGAGGGTC         [SEQ ID 3]

```
3' Primer
vgiawsp2  GTCGTGACCTGCGCCCC         [SEQ ID 4]

EXON3
5' Primer
vgiawsp3  GGGCGGGGCGGGGCTCGGG       [SEQ ID 5]
3' Primer
vgiawsp4  CGGGAGATCTACAGGCGATCAGG   [SEQ ID 6]

HLA-B

EXON2
5' Primer
vgibwsp3  TCCCACTCCATGAGGTAT        [SEQ ID 7]
3' Primer
vgibwsp4  GTCGTGACCTGCGCCCC         [SEQ ID 8]

EXON3
5' Primer
vgibwsp5  GGGCGGGGCGGGGCTCGGG       [SEQ ID 9]
3' Primer
vgibwsp6  GAAGGCTCCCCACTGCCC        [SEQ ID 10]

HLA-C

EXON2
5' Primer
vgicwsp3  GGAGGGTCGGGCGGGTCT        [SEQ ID 11]
3' Primer
vgicwsp4  GTCGTGACCTGCGCCCC         [SEQ ID 12]

EXON3
5' Primer
vgicwsp5  GACCGCGGGGCGGGGCCA        [SEQ ID 13]
          GACCACGGGGCGGGGCCA        [SEQ ID 14]
3' Primer
vgicwsp6  GAGGCTCCCCACTGCCC         [SEQ ID 15]
```

3 μl aliquots of the reaction mixture were placed into each of 4 tubes containing 3 μl of one of the following termination mixes containing all 4 dNTPs and one of the following ddNTPs: A, C, G or T (dNTP/ddNTP=100:1 ratio; 750 μM: 7.5 μM) after which the mixture was layered with oil. The mixture was then processed in a PTC 100 Thermocycler as follows:

denature
95° C. 120 sec
35 cycles
95° C. 50 sec
52° C. 30 sec
70° C. 60 sec
finish
70° C. 120 sec
6° C. soak 6 μl dye/stop solution was then added to each tube to make a final volume of 12 μl. 2 μl of final mixture was loaded on a lane of the MICROGENE BLASTER. 7 μl of final mixture was loaded on a lane of an ALF automated Sequencer (Pharmacia). Electrophoresis was performed and the separated reaction products were detected, recorded and evaluated.

The time saving of a single sequencing reaction of this type as compared to previously available sequencing methods is illustrated in Table 3.

TABLE 3

| Step | Prior Art Kit | Method of the Invention |
|---|---|---|
| PCR of natural abundance DNA | 2.5 hours | 0 |
| Purify Amplicon with | 1 hour | 0 |

TABLE 3-continued

| Step | Prior Art Kit | Method of the Invention |
|---|---|---|
| DYNAL Beads (optional) Sequencing Reactions | 2.5 hours | 2 hours |
| Total | 5 to 6 hours | 2 hours |

EXAMPLE 3

The presence of the sexually transmitted disease pathogen *Chlamydia trachomatis* in a patient sample is detected according to the method of the invention as follows.

Urine samples from patients suspected of carrying a sexually transmitted disease pathogen are prepared for sequence-based diagnosis as follows. 100 μl of first void urine are deposited in a sterile microcentrifuge tube. The tube is centrifuged at 12,000×g for 20 min; the supernatant is removed. 100 μl of Lysis Solution (Proteinase K @ 100g/ml; 1% Tween 20) is added to the bacterial pellet and incubated 1 h at 55° C., or 18 h at room temperature. After a final incubation at 95° C. for 10 minutes, 200 μl of GENECLEAN II glass milk is added, according to the manufacturer's instructions. (Bio 101, Inc) DNA is eluted in 10 μl of double distilled H$_2$O. (A lysis solution control may be prepared if desired, by adding the lysis solution to a sterile tube (a tube without any urine pellet), and treating this tube like the others.)

The sample natural abundance DNA is then treated according to the method of the invention with a pair of primers and reagents to identify the sequence of a *C. trachomatis* gene present in the sample, if any. A suitable *C. trachomatis* specific target for sequencing is the cryptic plasmid. Primers that may be used are

| Name | Sequence |
|---|---|
| KL1: | TCCGGAGCGA GTTACGAAGA [SEQ ID NO: 16] |
| KL2: | ATTCAATGCC CGGGATTGGT [SEQ ID NO: 17] |

These sequencing primers were employed previously for PCR amplification reactions, but not sequencing (Mahony et al., "Confirmatory polymerase chain reaction testing for *Chlamydia trachomatis* in first void urine from asymptomatic and symptomatic men" *J. Clin Microbiol.* 30:2241–2245 (1992)).

Both primers are labeled with spectroscopically-distinguishable labels. Labels are selected on the basis of the instrument employed for detection. Labeling reactions are performed according to methods well known in the art, such as amidite labeling or dye-ester condensation.

The sequencing reaction mixture is prepared by combining 2.5 μl of the prepared DNA sample, 0.67 μl of 10 μM primer KL1 (labeled with Cy5.5), 0.45 μl of KL2 primer at 10 μM, 2 μl of THERMO SEQUENASE reaction buffer (250 mM Tris-HCl pH 9.0 @ 25° C., 39 mM MgCl$_2$), 2 μl of THERMO SEQUENASE enzyme (Amersham Life Sciences) diluted 1/10 in the dilution buffer provided with the enzyme and 5.38 μl of double distilled H$_2$O. The final volume is 13 μl.

3 μl of the sequencing reaction mixture is placed in each of 4 clean tubes and covered with one drop of mineral oil (Sigma Chemical Co., Cat # M-5904). The tube is placed in a PTC-100 thermal cycler (M.J. Research, Maine) and heated for 3 min at 94° C., then cooled to 85° C. One of the following termination mixtures are then added to each of the 4 tubes:

- 3 μl of dNTP:ddATP (1 mM each dNTP, 3.3 μM ddATP) in tube A.
- 3 μl of dNTP:ddCTP (1 mM each dNTP, 3.3 μM ddCTP) in tube C.
- 3 μl of dNTP:ddGTP (1 mM each dNTP, 3.3 μM ddGTP) in tube G.
- 3 μl of dNTP:ddTTP (1 mM each dNTP, 3.3 μM ddTTP) in tube T.

The dNTP:ddNTP mixes are preferably heated to 85° C. when added to the tube. The reaction mixture is mixed well and it is subjected to the following thermal cycling regime for 55 cycles:

94° C./30 sec.
60° C./30 sec.
70° C./1 min

After the last cycle, the tubes are kept at 70° C. for 2 min, then cooled to 4° C. until ready for loading. To view the reaction products, 6 μl of loading buffer (dye/stop solution) is added to each tube. The aqueous phase (the bottom phase disposed under the oil layer) is removed and put it in another tube. The sample is heated to 75° C. for 3 min, and put on ice. 2 μl of each sample is loaded in each well of a MICROGENE BLASTER automated DNA sequencer (Visible Genetics Inc., Toronto, ON). The reaction products are electrophoretically separated and detected. The data is analyzed using GENEOBJECTS software (Visible Genetics Inc., Toronto, ON) to base-call (i.e. determine the DNA sequence) of the samples. The base-called sequence is compared to the known *C. trachomatis* sequence to confirm diagnosis. Results are reported to the patient file.

EXAMPLE 4

The method of the invention may be employed to identify not only the presence of *C. trachomatis* in a patient sample but also the strain identity. Health care workers currently seek to distinguish among *Chlamydia trachomatis* strains to determine the molecular epidemiologic association of a range of diseases with infecting genotype (See Dean, D. et al "Major Outer Membrane Protein Variants of *Chlamydia trachomatis* Are Associated with Severe Upper Genital Tract Infections and Histopathology in San Francisco." *J. Infect. Dis.* 172:1013–22 (1995)).

A suitable strain specific target for *C. trachomatis* is the omp1 (outer membrane protein) gene which has at least 4 variable sequence ("VS") domains that may be used to distinguish among the 15 known genotypes of *C. trachomatis* (Yuan, Y et al. "Nucleotide and Deduced Amino Acid Sequences for the Four Variable Domains of the Major Outer Membrane Proteins of the 15 *Chlamydia trachomatis* Serovars" Infect. Immun. 57 1040–1049 (1989)).

Because of the length of the VS domains, separate reactions are performed to obtain sequence from VS1/VS2 and VS3/VS4 as a basis for strain identification. The following oligonucleotide primers, each labeled with a spectroscopically-distinguishable label may be employed:

For VS1/VS2:

| Name | Sequence | |
|---|---|---|
| MF21 | CCGACCGCGT CTTGAAAACA GATGT | [SEQ. ID NO. 18] |
| MB22 | CACCCACATT CCCAGAGAGC T | [SEQ. ID NO. 19] |

For VS3/VS4

| Name | Sequence | |
|---|---|---|
| MVF3 | CGTGCAGCTT TGTGGGAATG T | [SEQ. ID NO. 20] |
| MB4 | CTAGATTTCA TCTTGTTCAA TTGC | [SEQ. ID NO. 21] |

Strain-specific *C. trachomatis* identification over the VS1/VS2 domain can also be achieved using the following degenerate primers sets:

```
Forward
OMP291: AGCATGCGTR TKGGTTACTA YGG [SEQ ID NO. 22]
(labeled with Cy5.5). Base 175 to 197 of the ORF
of the omp1 gene of C. trachomatis.

Forward
OMP314A: TGACTTTGTT TTCGACCGYG TTTT [SEQ ID NO. 23]
(labeled with Cy5.5). Base 198 to 221 of the ORF
of the omp1 gene of C. trachomatis.

Reverse
OMP722: CTAAAGTYGC RCATCCACAT TCC [SEQ ID NO. 24]
(labeled with a spectroscopically-distinguishable
label) Base 637 to 615 of the ORF of the omp1 (in
serovar K) gene of C. trachomatis. The primer may
not have the exact same sequence as in serovar K.

Reverse
OMP711: CATCCACATT CCCASARAGC TGC [SEQ ID NO. 25]
```

(labeled with a spectroscopically-distinguishable label) Base 626 to 604 of the ORF of the omp1 (in serovar K) gene of *C. trachomatis*. The primer may not have the exact same sequence as in serovar K.

These primers sets are preferably used in the following combinations:

(1) OMP291–OMP722, sequencing a 455 to 463-bp (depending on the serotype) fragment of the omp1 gene of *C. trachomatis*; or (2) OMP314A–OMP711, sequencing a 421 to 430-bp (depending on the serotype) fragment of the omp1 gene of *C. trachomatis*.

The use of two labels in these methods is a substantial improvement over single-label cycle sequencing or two-label non-cycled sequencing. The method takes advantage of the fact that a given termination mixture containing, for example, ddATP will give chain termination products for the A nucleotide in both directions. The different primer labels means that one reaction mixture loaded in a single lane of an automated DNA sequencing apparatus designed to detect the two labels (a "multi-dye sequencer") will identify the A nucleotide of both sense and antisense strands. Separate reactions are performed for the other 3 nucleotides. Using only 4 lanes of an electrophoresis gel, and 4 reaction mixtures, the DNA sequences of both the sense and antisense strands can be obtained. This information allows the operator to resolve any ambiguities that may be present.

Use of two different labels lends itself to a further improvement. As noted above, in a reaction according to the invention, the results of the ddATP reaction will give chain termination products for the A nucleotide in both directions. Since the A nucleotide in one direction corresponds to the T nucleotide in the other, a single reaction can provide the location of two bases. A second termination reaction with, for example, ddCTP will then obtain the positions of the other two nucleotides, C and G. Thus only two lanes of an electrophoresis gel and 2 reaction mixtures are required to identify the location of all 4 bases of the sequence.

A suitable multi-dye sequencer for use with this aspect of the invention, is the Applied Biosystems 377 PRISM automated DNA sequencer (Applied Biosystems Inc., Foster City, Calif.). The fluorescent labels are selected to be detectable on the 377 instrument. Instead of the dye-terminator chemistry suggested in the Applied Biosystems product literature, however, the fluorescent labels must be conjugated to the 5' end of the primer molecules. The samples are electrophoresed, detected and the detected data is recorded.

Sophisticated software such as GENEOBJECTS software (Visible Genetics Inc, Toronto, Calif.) may be used to assist in evaluation of the results. This software may employ the methods of commonly assigned U.S. patent applications Ser. Nos. 08/497,202 and 08/670,534 and International Patent Application No. PCT/US96/11130, all of which are incorporated herein by reference. In one of the methods, the single nucleotide data tracks are evaluated and nucleotides are positioned relative to the known (or standard) DNA sequence expected from the sample. When data tracks are generated for each of the four nucleotides, the full DNA sequence of the sample may be base-called. The base-called sequence is then compared to the library of known sequences to determine which C. trachomatis strain or strains are present in the sample.

EXAMPLE 5

The sequence of both the sense strand and antisense strand of a C. trachomatis cryptic plasmid gene may be obtained in a one step reaction using the primers:

| Name | Sequence | | |
|---|---|---|---|
| KL1: | TCCGGAGCGA GTTACGAAGA | [SEQ ID NO. 16] | |
| CT1590: | ATGCCCGGGA TTGGTTGATC | [SEQ ID NO. 26] | |

Combine the following materials and mix well:

| | Concentration | Amount |
|---|---|---|
| Patient Sample DNA | | 11.25 ul |
| KL1*Cy5.5 Primer | 10 uM | 3 ul |
| CT1590* Fluorescein Primer | 10 uM | 2 ul |
| Enzyme Diluent (Amersham plc) | | 8 ul |
| THERMO SEQUENASE Enzyme | 32 U/ul | 0.9 ul |
| double distilled H$_2$O | | 24.2 ul |

Take 11 µl of the mixture and add 2 µl of 13X buffer [Tris-HCl 260 mM pH 8.3, MgCl$_2$ 39 mM] (final concentration 20 mM Tris-HCl pH 8.3, 3 mM MgCl$_2$). Mix well and place 3 µl into each of 4 tubes. Heat tube to 94° C. for 5 mins then reduce temperature to 85° C. Add and mix 3 µl of an 85 C. dNTP/ddNTP solution consisting of 0.75 mM each dNTP and 2.5 µM of a chain terminating nucleotide triphosphate (ddNTP) (use a different ddNTP in each of the 4 tubes).

Treat the mixture to 60 cycles of the following thermal cycling reactions: 94° C. for 10 sec, 62° C. for 15 sec, 70° C. for 1 min. Upon completion, treat the mixture for a final 5 min at 70 C. and then store at 4° C. until ready for loading. For viewing the reaction products, add an equal volume of stop/loading solution (95% formamide plus a colored dye).

Take 1.5 µl and load in a single lane of a MICROGENE BLASTER automated DNA sequencer (Visible Genetics Inc., Toronto). Load the remaining mixture (@ 10.5 µl) in a single lane of an ALF Automated Sequencer (Pharmacia LKB, Uppsala, Sweden). The reaction products from the Cy5.5 labeled primer are detected on the MICROGENE BLASTER using GENEOBJECTS Software. The reaction products from the fluorescein labeled primer are detected on the ALF Automated Sequencer using GENEOBJECTS Software. The base-calling results of the Cy5.5 labeled primer were compared to the known sequence of the gene by the GENELIBRARIAN component of GENEOBJECTS.

EXAMPLE 6

As described in U.S. patent application Ser. No. 08/577,858 (now U.S. Pat. No. 5,834,189), not all 4 nucleotides of C. trachomatis, or any polymorphic or multiple allelic locus of any gene or organism necessarily need to be determined in order to ascertain which allele or variant is present. In many cases, positioning less than four nucleotides may be sufficient to determine with certainty which allele is present. The method of Example 4 may be modified to obtain single nucleotide data tracks (or fragment patterns) by performing only one of the termination reactions at a time.

In the case of detection and serotyping of C. trachomatis, the evaluation of the A track alone over the first 100 nucleotides of the omp1 gene, aligning to nucleotides 249–349 of the serovars C and K, can distinguish the serovars. Appendix I of Ser. No. 08/577,858 is a text file representation of the omp1 gene in each of the serovars. The sequences are all aligned to the last (3') nucleotide of the detectably labeled primer omp314A. (Appendix I shows sequences starting 29 bp downstream of the 3'-nucleotide.) This illustration differs from a traditional "consensus" sequence illustrations in that all missing bases (usually represented by N's or raised dashes) are deleted. The A's are illustrated in the order and positions in which they would be expected to appear after a sequencing reaction and upon detection by an automated DNA electrophoresis apparatus.

If, in another microorganism, the A lane (or other preferred first lane) were not sufficient to distinguish all types, a second reaction for the C, G or T nucleotide could be performed to further define the qualitative nature of any target microorganism present in the sample. Because the sequences of the types are previously known, the operator can determine which of the nucleotides provide the greatest information and will analyze those nucleotides first.

EXAMPLE 7

The presence of and strain identity of C. trachomatis in a patient sample may be determined according to the methods of the previous examples by substituting the following primer pairs. These primers are used to determine the sequence of the omp1 gene (publicly available at GENBANK Accession No. X62921).

```
Forward Primer (5' Primer) labeled with a
detectable label such as Cy5.5:

Primer OMP312: GGAGACTTTG TTTTCGACCG [SEQ ID NO 27]
Position 312-331 of X62921 and one of the following Reverse Primers
(3' Primer) (labeled with a detectable label
different from the 5' primer):
```

-continued

Primer OMP708: CATTCCCACA AAGCTGCGCG [SEQ ID NO 28]
Position 727-708 of X62921

Primer OMP706: TTCCCACAAA GCTGCGCGAG [SEQ ID NO 29]
Position 725-706 of X62921

Primer OMP704: CCCACAAAGC TGCGCGAGCG [SEQ ID NO 30]
Position 723-
704 of X62921

The following combination can be used to
obtain DNA sequence over the following maximum
lengths:
OMP312-OMP708: 416-nt region of omp1
OMP312-OMP706: 414-nt region of omp1
OMP312-OMP704: 412-nt region of omp1

EXAMPLE 8

The sequence of both the sense strand and antisense strand of the protease gene of HIV-1 integrated into natural abundance DNA of lymphocytes may be obtained in a one step reaction as follows.

Natural abundance DNA is prepared from the patient blood lymphocyte sample according to a standard method such as a standard salting-out procedure (as provided by the PUREGENE DNA Isolation Kit, Gentra Systems, Inc., Minneapolis) or by detergent and proteinase K treatment (Current Protocols in Molecular Biology, Eds. Ausubel, F. M. et al, (John Wiley & Sons; 1995)).

Combine the following materials and mix well:

|  | Concentration | Amount |
|---|---|---|
| Patient Sample DNA |  | 11.25 ul |
| PR211F*Cy5.5 Primer | 10 uM | 3 ul |
| or |  |  |
| PR281*Cy5.5 Primer | 10 uM | 3 ul |
| PR526* Fluorescein Primer | 10 uM | 2 ul |
| Enzyme Diluent (Amersham plc) |  | 8 ul |
| THERMO SEQUENASE Enzyme | 32 U/ul | 0.9 ul |
| double distilled H$_2$O |  | 24.2 ul |

The primers have the following sequences:

```
Name    Sequence
Choice of Forward Primers
PR211F ATCACTCTTT GGCAACGACC       [SEQ ID No. 31]
(FORWARD), BASE 6 TO 25 OF THE PROTEASE GENE PR281  CAGGAGCAGA TGATACAGTA TTAG  [SEQ ID No. 32]
(FORWARD), BASE 76 TO 99 OF THE PROTEASE GENE Reverse Primer
PR526: CCATTCCTGG CTTTAATTTT ACTGG [SEQ ID No. 33]
(REVERSE), BASES 321 TO 345 OF THE PROTEASE GENE
```

PR211F-PR526 creates a sequencing fragment of maximum size 340 bp. PR281-PR526 creates a sequencing fragment of maximum size 270 bp. Both regions contain the sequence of the various codons where mutations are involved in protease inhibitor resistance (Codons 46, 48, 54, 63 82 84 and 90).

Take 11 μl of the mixture and add 2 μl of 13X buffer [Tris-HCl 260 mM pH 8.3, MgCl$_2$ 39 mM] (final concentration 20 mM Tris-HCl pH 8.3, 3 mM MgCl$_2$). Mix well and place 3 μl into each of 4 tubes. Heat tube to 94 C. for 5 mins then reduce temperature to 85 C. Add and mix 3 μl of an 85 C. dNTP/ddNTP solution consisting of 0.75 mM each dNTP and 2.5 μM of a chain terminating nucleotide triphosphate (ddNTP) (use a different ddNTP in each of the 4 tubes).

Treat the mixture to 60 cycles of the following thermal cycling reactions: 94 C. for 10 sec, 62 C. for 15 sec, 70 C. for 1 min. Upon completion, treat the mixture for a final 5 min at 70 C. and then store at 4 C. until ready for loading. For viewing the reaction products, add an equal volume of stop/loading solution (95% formamide plus a colored dye). Take 1.5 μl and load in a single lane of a MICROGENE BLASTER automated DNA sequencer (Visible Genetics Inc., Toronto). Load the remaining mixture (@ 10.5 μl) in a single lane of an ALF Automated Sequencer (Pharmacia LKB, Uppsala, Sweden). The reaction products from the Cy5.5 labeled primer are detected on the MICROGENE BLASTER using GENEOBJECTS Software. The reaction products from the fluorescein labeled primer are detected on the ALF Automated Sequencer using GENEOBJECTS Software. The base-called results from each primer were compared to the known sequences of HIV-1 by GENELIBRARIAN (a component of GENEOBJECTS (Visible Genetics Inc, Toronto).

We claim:

1. A method for simultaneously determining the positions of a selected nucleotide base in a target region of both strands of a denatured duplex nucleic acid polymer comprising the steps of:

(a) combining the nucleic acid polymer with a reactant mixture comprising first and second oligonucleotide primers, said primers binding to the sense and antisense strands, respectively, of the nucleic acid polymer at a location flanking the target region, a thermostable DNA polymerase, a chain-terminating nucleotide triphosphate complementary to the selected nucleotide base, and reagents for synthesis of chain extension products to form a reaction mixture;

(b) processing the reaction mixture through a plurality of thermal cycles, each including at least a chain extension phase and a denaturation phase to produce chain extension products;

(c) evaluating the chain extension products to determine the positions of the selected bases, wherein the first and second oligonucleotide primers are each labeled with different, spectroscopically distinguishable fluorescent labels.

2. The method according to claim 1, wherein the reaction mixture comprises a thermally-stable polymerase enzyme which incorporates dideoxynucleotides into an extending nucleic acid polymer at a rate which is no less than 0.4 times the rate of incorporation of deoxynucleotides.

3. The method according to claim 2, wherein the sample is a natural abundance sample which has not been subjected to a preferential purification or amplification step to increase the amount of target DNA relative to non-target DNA present in the initial sample.

4. The method of claim 2, wherein the mole ratio of the dideoxynucleotide triphosphate to the corresponding deoxynucleotide triphosphate in the reaction mixture is from 1:50 to 1:1000.

5. The method of claim 4, wherein the mole ratio of the dideoxynucleotide triphosphate to the corresponding deoxynucleotide triphosphate is from 1:100 to 1:300.

* * * * *